United States Patent
Kohler et al.

(10) Patent No.: US 7,672,490 B2
(45) Date of Patent: Mar. 2, 2010

(54) MOTION ARTIFACTS COMPENSATION

(75) Inventors: Thomas Kohler, Norderstedt (DE); Roland Proksa, Hamburg (DE); Claas Bontus, Hamburg (DE)

(73) Assignee: Koninklijke Philips Electronics N.V., Eindhoven (NL)

(*) Notice: Subject to any disclaimer, the term of this patent is extended or adjusted under 35 U.S.C. 154(b) by 871 days.

(21) Appl. No.: 10/597,871

(22) PCT Filed: Feb. 4, 2005

(86) PCT No.: PCT/IB2005/050466
§ 371 (c)(1),
(2), (4) Date: Aug. 10, 2006

(87) PCT Pub. No.: WO2005/078664
PCT Pub. Date: Aug. 25, 2005

(65) Prior Publication Data
US 2007/0177713 A1  Aug. 2, 2007

(30) Foreign Application Priority Data
Feb. 13, 2004  (EP) ................... 04100555

(51) Int. Cl.
*G06K 9/00* (2006.01)
*A61B 6/00* (2006.01)
*A61B 5/05* (2006.01)

(52) U.S. Cl. ............................. 382/128; 378/4; 600/407

(58) Field of Classification Search ................. 382/128, 382/129, 130, 131, 132, 133, 134; 378/4, 378/8, 21–27, 90, 92, 98.4, 98.6, 98.9, 101, 378/140, 901; 128/920, 922; 348/154, 155; 600/407, 410, 411, 425, 524
See application file for complete search history.

(56) References Cited

U.S. PATENT DOCUMENTS

| | | | | | |
|---|---|---|---|---|---|
| 5,148,032 | A | * | 9/1992 | Hernandez | ............... 250/492.1 |
| 5,671,263 | A | * | 9/1997 | Ching-Ming | ................... 378/8 |
| 6,215,841 | B1 | * | 4/2001 | Hsieh | ............................. 378/8 |
| 2002/0037068 | A1 | * | 3/2002 | Oikawa | ....................... 378/15 |
| 2002/0172321 | A1 | | 11/2002 | Sembritzki et al. | |
| 2002/0186871 | A1 | | 12/2002 | Grass et al. | |
| 2003/0142778 | A1 | | 7/2003 | Proksa | |

FOREIGN PATENT DOCUMENTS

WO  03/045247 A1  6/2003

OTHER PUBLICATIONS

Koken, P., et al.; Motion Artefact Reduction for Exact Cone-Beam CT Reconstruction Algorithms; 2004; IEEE Nuclear Science Symposium Conference Record; 5:2985-2988.
Linney, N.C., et al.; Organ Motion Detection in CT Images Using Opposite Rays in Fan-Beam Projection Systems; 2001; IEEE Trans. On Medical Imaging; 20(11)1109-1122.

* cited by examiner

*Primary Examiner*—Abolfazl Tabatabai

(57) ABSTRACT

Motion is one of the most critical sources of artifacts in helical conebeam CT. By comparing opposite rays corresponding to projection data, the amount of motion may be estimated and, in the following suppression of corresponding motion artifacts may be performed according to an exemplary embodiment of the present invention. The method of motion artifact compensation may be implemented in both approximate reconstruction algorithms and exact reconstruction algorithms. Advantageously, motion during the data acquisition is detected automatically and related motion artifacts may be suppressed adaptively.

20 Claims, 11 Drawing Sheets

MOTION ARTIFACTS COMPENSATION

The present invention relates to the field of image processing, for example, in medical applications. In particular, the present invention relates to a method of motion artifact compensation in a projection data set, to data processing devices and to respective computer programs.

In a CT scanner with a polychromatic source of radiation, such as a polychromatic x-ray source, a polychromatic x-ray beam passes through matter and photons are absorbed or scattered according to the properties of the matter they are passing through. The introduction of cone-beam computer tomography (CT) systems offers a couple of benefits. Compared with a single slice CT system, the time for data acquisition can be reduced, the output of the x-ray tube is used more efficiently, leading to a simpler heat management of the tube, and there is no longer a need for compromising z-resolution in order to achieve an acceptable scan time. However, a major problem using cone-beam CT systems is to find a proper reconstruction algorithm. A large number of publications within the last few years has addressed the problem of reconstruction of cone-beam projections acquired during a helical path of the source-detector system. Thus far, exact or quasi-exact algorithms exist only for a PI and a 3-PI-acquisition. Alternatively, an approximate algorithm may be used, such as PI-FBP, WEDGE or WEDGE-PI.

Motion is one of the most critical sources of artifacts in helical cone-beam CT. This is especially true if state of the art exact methods are used for reconstruction. Typically, these methods use an angular range of exactly n-PI of projection data for the reconstruction of each object point. This feature implies that the first and last ray used for reconstruction of a certain object point are exactly the same, but taken from opposite sides. Motion artifacts appear as arcs, which are due to an inconsistency between the first and the last ray. Approximate methods, like WEDGE mitigate this problem by so-called over-scan weighting. In this case, a trade-off between good suppression of motion artifacts by using a large over-scan range and best image quality for the static case by using a small over-scan range has to be found.

It is an object of the present invention to provide for an improved motion artifact compensation.

In accordance with an exemplary embodiment of the present invention as set forth in claim 1, the above object may be solved by a method of motion artifact compensation in a projection data set of an object of interest, wherein the projection data set is acquired by means of a source of electromagnetic radiation generating a beam and by means of a radiation detector detecting the beam. According to this exemplary embodiment of the present invention, a difference of the projection data of the first ray and the projection data of the second ray is determined, after which the projection data set is compensated for a motion artifact on the basis of the difference, resulting in a motion artifact compensated projection data set. After that, the object of interest is reconstructed from the motion artifact compensated projection data set, resulting in a motion artifact compensated image. The first ray and the second ray create projection data of the projection data set. The first ray and the second ray are opposite rays passing through a single object point and the difference of the projection data of the first ray and the projection data of the second ray is due to the motion of the object of interest resulting in motion artifacts.

In other words, an image is taken from an object of interest and projection data, which has been measured twice (for the first time by the first ray and for the second time by the second opposing ray both passing through a single object point) are compared to each other. If a difference is determined between the projection data resulting from the first ray and the second ray, the projection data set is compensated for a motion artifact, depending on the difference. After motion artifact compensation, a reconstruction of the object of interest is performed on the basis of the motion artifact compensated projection data set.

Further, as set forth in claim 11, a data processing device is provided, which comprises a memory for storing a data set and a data processor for performing motion artifact compensation in a projection data set of an object of interest, wherein the data processor is adapted for performing the following operation: loading the data set acquired by means of a rotating source of electromagnetic radiation generating a beam and by means of a radiation detector detecting the beam; determining a difference between the projection data of the first ray and the projection data of the second ray of the beam; compensating the projection data set for a motion artifact on the basis of the difference, resulting in a motion artifact compensated projection data set; and reconstructing the object of interest from the motion artifact compensated projection data set, resulting in a motion artifact compensated image. The first ray and the second ray create projection data of the projection data set and are opposite rays passing through a single object point. Furthermore, the difference between the projection data of the first ray and the projection data of the second ray is due to the motion of an object of interest resulting in motion artifacts.

Advantageously, this may allow for improved image quality of images comprising motion artifacts.

The present invention also relates to a computer program, which may, for example, be executed on a processor, such as an image processor. Such computer programs may be part of, for example, a CT scanner system. The computer programs, according to an exemplary embodiment of the present invention, are set forth in claim 12. These computer programs may be preferably loaded into working memories of data processors. The data processors are thus equipped to carry out exemplary embodiments of the methods of the present invention. The computer programs may be stored on a computer readable medium, such as a CD-ROM. The computer programs may also be presented over a network such as the World-WideWeb, and may be downloaded into the working memory of a data processor from such networks.

Advantageously, comparing the projection data resulting from the first ray and the projection data resulting from the second ray may be performed automatically during the scan, which may lead to a fast motion artifact compensation.

According to another exemplary embodiment of the present invention as set forth in claim 2, the determination of a difference between the first ray and the second ray further comprises the steps of selecting the first ray and the second ray on the basis of the projection data and determining whether the difference between the first ray and the second ray is greater than a predetermined threshold, wherein, if the difference is greater than the predetermined threshold, a motion artifact compensation of the projection data set is performed.

Advantageously, according to this exemplary embodiment of the present invention, no motion artifact compensation of the projection data set is performed if the difference between the first ray and the second ray does not exceed the predetermined threshold value. Therefore, by selecting a certain threshold value, the sensitivity of the motion artifact compensation algorithm may be set according to individual needs.

Another exemplary embodiment of the present invention is set forth in claim 3, wherein the second ray is interpolated from adjacent rays. Therefore, even if there is no original second ray which is exactly opposite to the first ray, such a second ray may be generated by interpolation from adjacent rays, which may be rays corresponding to projection data acquired in the neighborhood of the interpolated projection data corresponding to the interpolated second ray.

According to another exemplary embodiment of the present invention as set forth in claim 4, the object of interest comprises a plurality of object points, wherein a reconstruction of a first object point of the plurality of object points is performed by an exact reconstruction algorithm. Furthermore, if the motion artifact results from a motion of the first object point, the motion artifact is compensated for by a low pass filtering of the projection data in the region of the motion artifact before the reconstruction of the first object point by the exact reconstruction algorithm.

Advantageously, according to this exemplary embodiment of the present invention, this may smear out inconsistency over a large area and may thus result in a less severe motion artifact.

According to another exemplary embodiment of the present invention as set forth in claim 5, the source of radiation moves around the object of interest and the exact reconstruction algorithm uses projection data resulting from one of half a revolution and three half revolutions of the source of radiation.

Advantageously, by using projection data resulting from half a revolution of the source of radiation, opposing first and second rays may be easily and quickly detected, even with small detector arrays.

Another exemplary embodiment of the present invention is set forth in claim 6, wherein characteristics of the low-pass filtering correspond to properties of the projection data in the region of the motion artifact. Advantageously, according to this exemplary embodiment of the present invention, a filter threshold may be dynamically selected, depending on the severity of the motion artifact.

According to another exemplary embodiment of the present invention as set forth in claim 7, the object of interest comprises a plurality of object points, wherein a reconstruction of a first object point is performed by an approximate reconstruction algorithm. An over-scan range is used for reconstruction of the first object point. If the motion artifact results from a motion of the first object point, the motion artifact is compensated for by increasing the over-scan range. Advantageously, this procedure allows for a local optimization of the image quality.

According to another exemplary embodiment of the present invention as set forth in claim 8, the first object point belongs to a PI-line, on which motion has been detected and the increase of the over-scan range corresponds to properties of the projection data in the region of the motion artifact. Advantageously, according to this exemplary embodiment of the present invention, the over-scan range may be set according to the severity of the motion artifact. In other words, a rather dominant motion artifact may lead to a large over-scan range and a smaller motion artifact may lead to a small over-scan range. This dynamic setting of the over-scan range on the basis of, for example, the difference between the first ray and the second ray, may lead to a fast and individual motion artifact compensation.

According to another exemplary embodiment of the present invention as set forth in claim 9, the approximate reconstruction algorithm is one of a WEDGE algorithm and a PI-filtered back projection algorithm (PI-FBP). Thus, a high sensitivity for motion artifacts may be achieved.

According to another exemplary embodiment of the present invention as set forth in claim 10, the source of electromagnetic radiation is a polychromatic x-ray source, which moves along a helical path around the object of interest. Furthermore, the beam has one of a cone beam geometry and a fan beam geometry.

The application of polychromatic x-rays is advantageous, since polychromatic x-rays are easy to generate and provide a good image resolution. Furthermore, since the geometry of the CT scanner system may be of different designs, such as, for example, cone beam or fan beam geometry, a method for an exemplary embodiment of the present invention may be applied to a plurality of different scanner systems and may not be limited to CT scanner systems.

It may be seen as the gist of an exemplary embodiment of the present invention that motion artifacts in a projection data set are detected by determining a difference between a first ray and a second ray, which are opposite to each other and create projection data, which do not show a difference in the absence of motion. After determining the difference, the projection data set is compensated for a motion artifact depending on the magnitude of the difference. This may provide for a better image quality in reconstructed images.

These and other aspects of the present invention will become apparent from and elucidated with reference to the embodiments described hereinafter.

Exemplary embodiments of the present invention will be described in the following, with reference to the following drawings:

FIG. 1 shows a simplified schematic representation of an embodiment of a computed tomography (CT) scanner according to the present invention.

FIG. 2*a* shows a schematic representation of a virtual planar detector according to a cone beam reconstruction.

FIG. 2*b* shows a parallel beam geometry according to a PI-FBP algorithm.

Figure 10A:
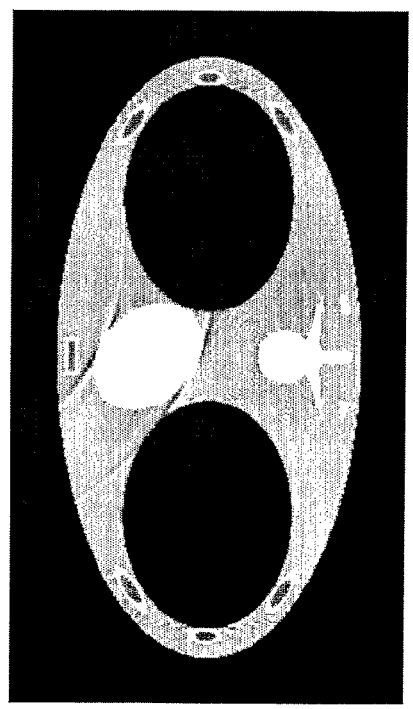

FIG. 10*a* shows a reconstructed axial slice for a moving heart, which is not compensated for motion artifacts according to the present invention.

Figure 10B:
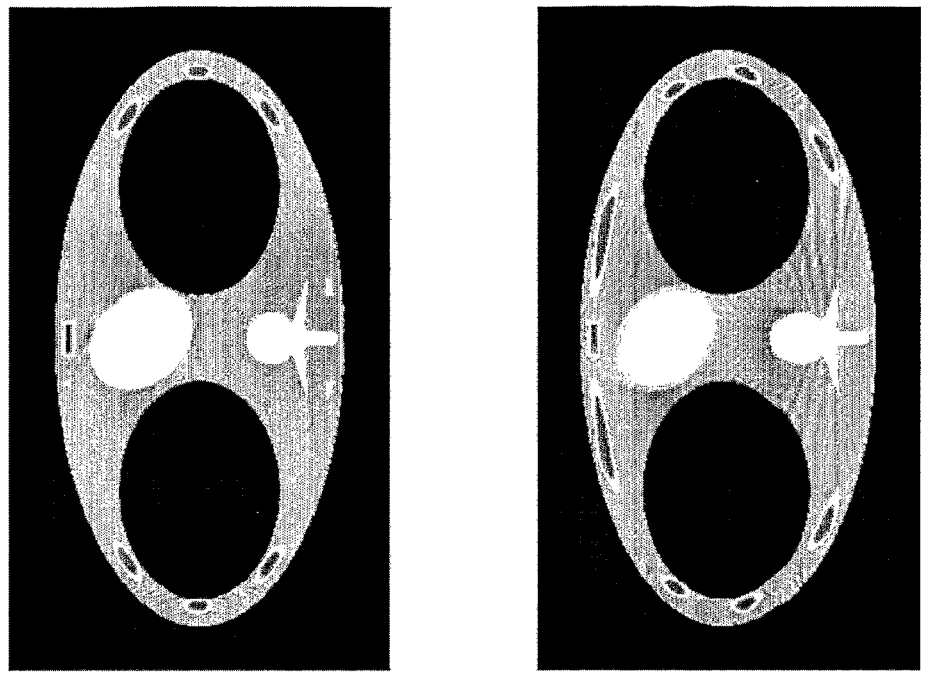

FIG. 10*b* shows two reconstructed axial slices with the PI+plus+EPSELON algorithm for the moving heart.

Figure 11:
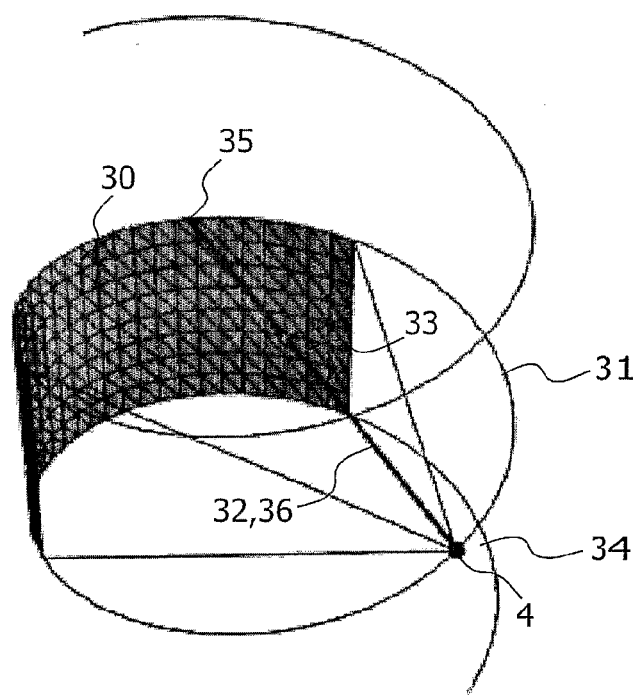

FIG. 11 shows a schematic representation of a PI-line.

Figure 12:
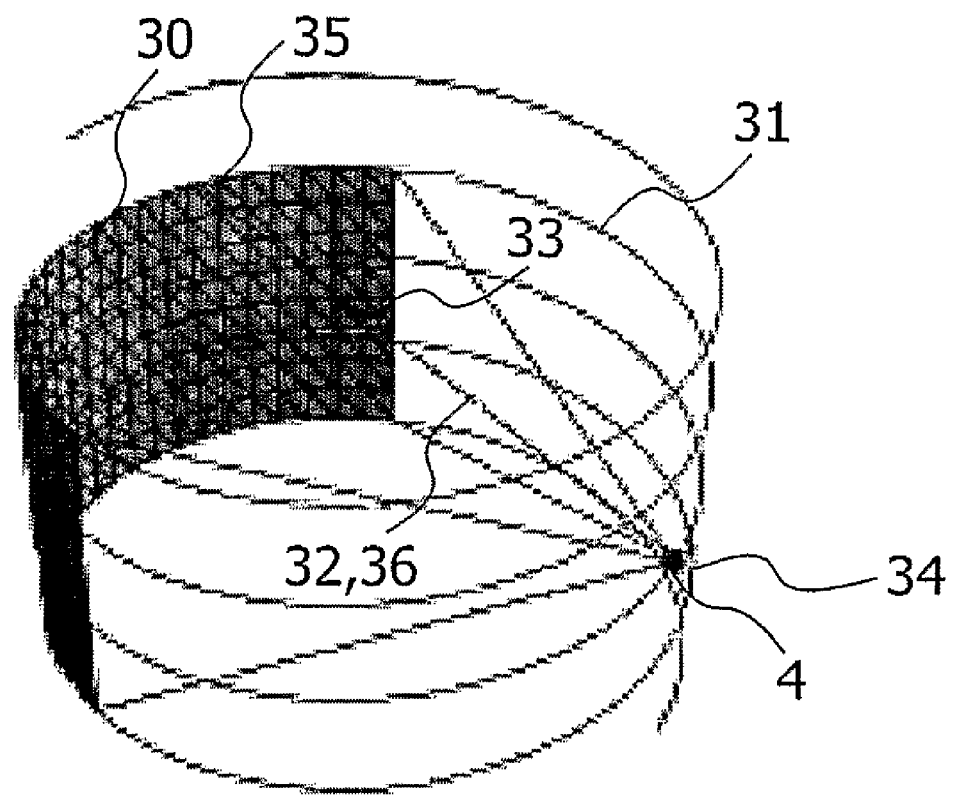

FIG. 12 shows a schematic representation of a 3 PI-line.

Figure 13:
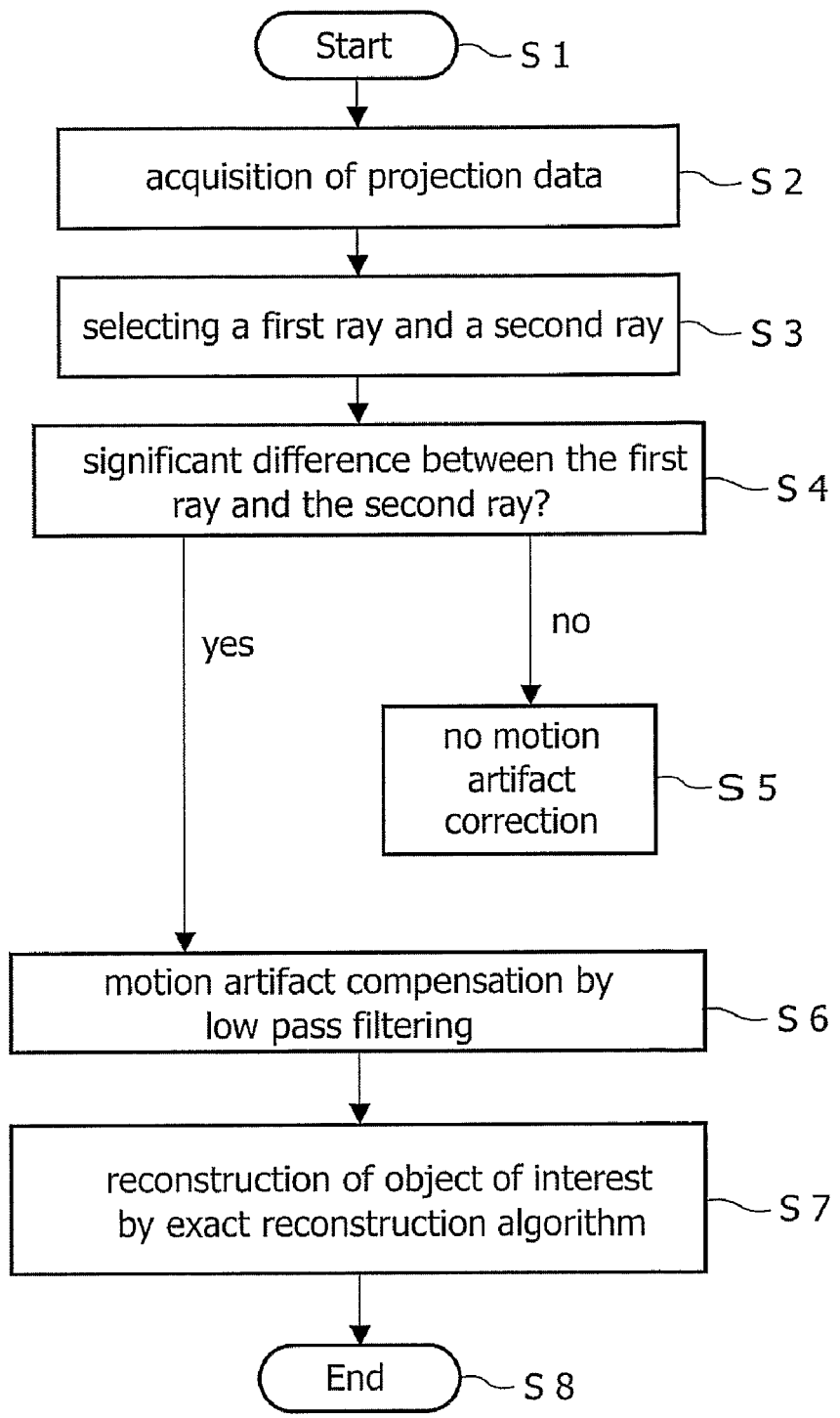

FIG. 13 shows a flow-chart of an exemplary embodiment of method of motion artifact compensation according to the present invention.

Figure 14:
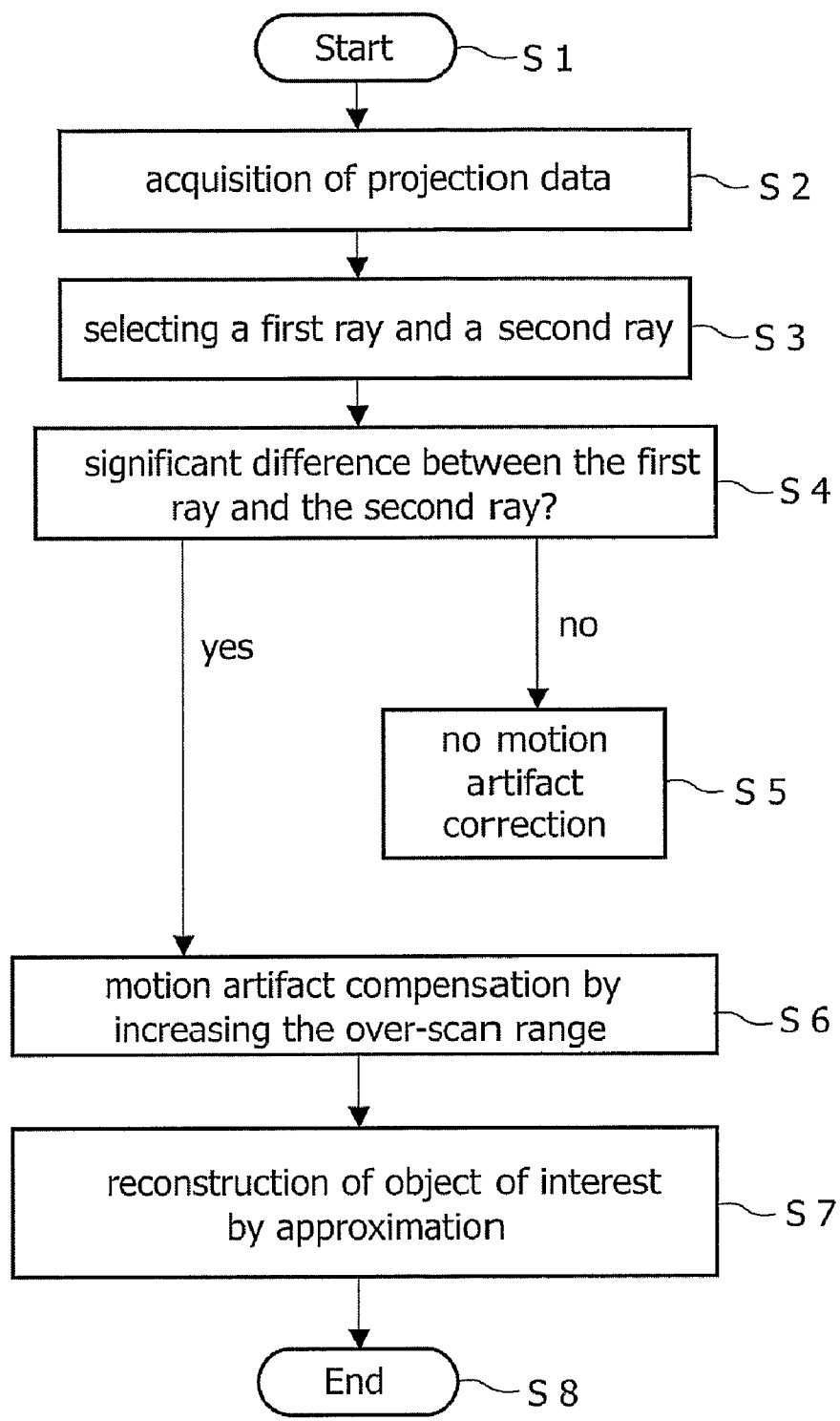

FIG. 14 shows a flow-chart of another exemplary embodiment of a method of motion artifact compensation according to the present invention.

Figure 15:
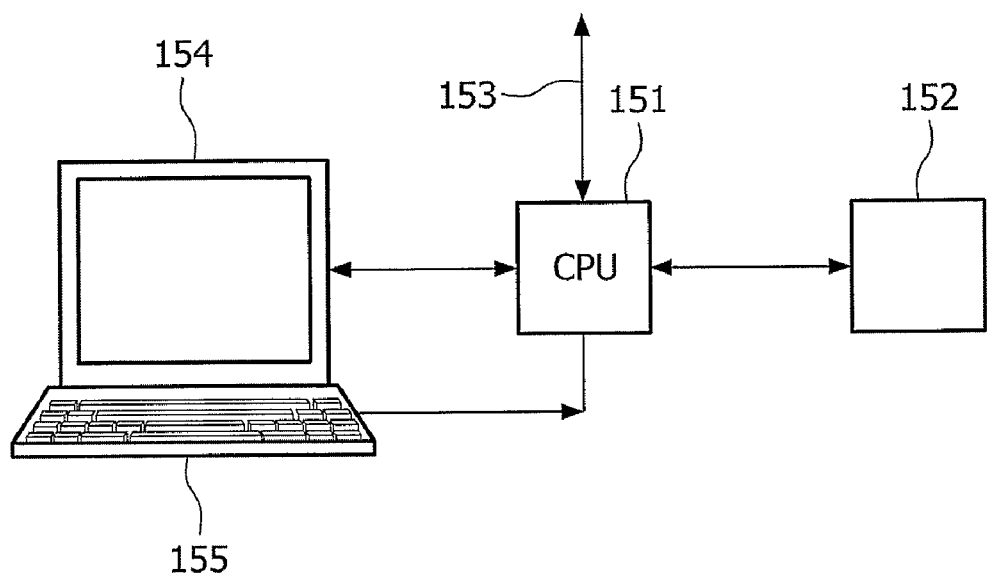

FIG. 15 shows an exemplary embodiment of an image processing device according to the present invention for executing an exemplary embodiment of a method in accordance with the present invention.

Figure 1:
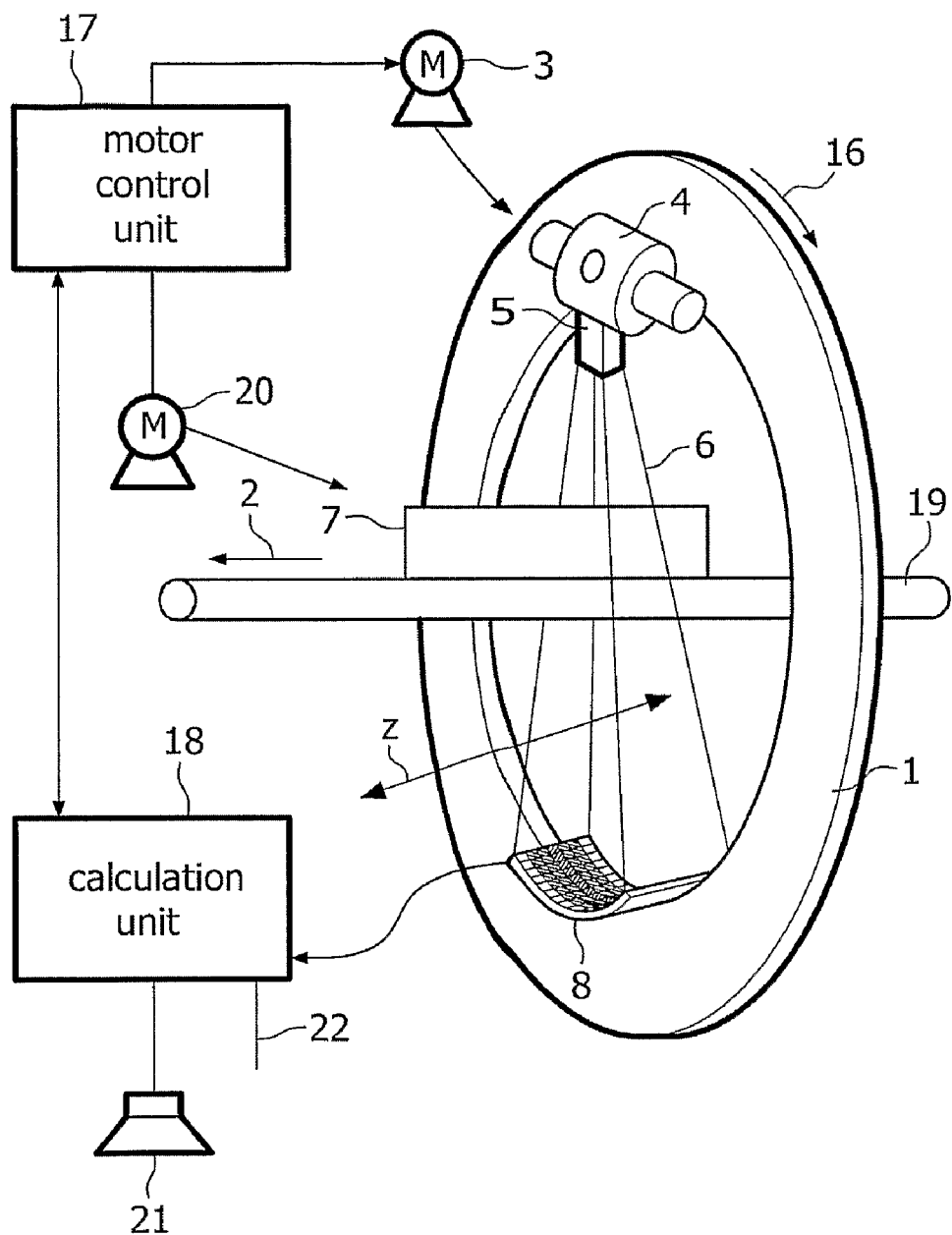

FIG. 1 shows an exemplary embodiment of a CT (computed tomography) scanner system according to the present invention. With reference to this exemplary embodiment, the present invention will be described for the application in medical imaging. However, it should be noted that the present invention is not limited to the application in the field of medical imaging, but may be used in applications such as baggage inspection to detect hazardous materials, such as explosives, in items of baggage or other industrial applications, such as material testing.

The scanner depicted in FIG. 1 is a cone beam CT scanner. The CT scanner depicted in FIG. 1 comprises a gantry 1, which is rotatable around a rotational axis 2. The gantry is driven by means of a motor 3. Reference numeral 4 designates a source of radiation such as an x-ray source, which, according to an aspect of the present invention, emits a polychromatic radiation.

Reference numeral 5 designates an aperture system which forms the radiation beam emitted from the radiation source to a cone shaped radiation beam 6.

The cone beam 6 is directed such that it penetrates an object of interest 7 arranged in the center of the gantry 1, i.e. in an examination region of the CT scanner and impinges onto the detector 8. As may be taken from FIG. 1, the detector 8 is arranged on the gantry 1 opposite the source of radiation 4, such that the surface of the detector 8 is covered by the cone beam 6. The detector 8 depicted in FIG. 1 comprises a plurality of detector elements.

During a scan of the object of interest 7, the source of radiation 4, the aperture system 5 and detector 8 are rotated along gantry 1 in the direction indicated by arrow 16. For rotation of the gantry 1 with the source of radiation 4, the aperture system 5 and the detector 8, the motor 3 is connected to a motor control unit 17, which is connected to a calculation unit 18.

In FIG. 1, the object of interest is disposed on a conveyor belt 19. During the scan of the object of interest 7, while the gantry 1 rotates around the patient 7, the conveyor belt 19 displaces the object of interest 7 along a direction parallel to the rotational axis 2 of the gantry 1. By this, the object of interest 7 is scanned along a helical scan path. The conveyor belt 19 may also be stopped during the scans to thereby measure single slices. Instead of providing a conveyor belt 19, for example, in medical applications, where the object of interest 7 is a patient, a movable table is used. However, it should be noted that in all of the described cases it is also possible to perform a circular scan, where there is no displacement in a direction parallel to the rotational axis 2, but only the rotation of the gantry 1 around the rotational axis 2.

The detector 8 is connected to the calculation unit 18. The calculation unit 18 receives the detection result, i.e. the read-outs from the detector element of the detector 8, and determines a scanning result on the basis of the read-outs. The detector elements of the detector 8 may be adapted to measure the attenuation caused to the cone beam 6 by the object of interest. Furthermore, the calculation unit 18 communicates with the motor control unit 17 in order to coordinate the movement of the gantry 1 with motor 3 and 20 or with the conveyor belt 19.

The calculation unit 18 may be adapted for reconstructing an image from read-outs of the detector 8. The image generated by the calculation unit 18 may be output to a display (not shown in FIG. 1) via an interface 22.

The calculation unit, which may be realized by a data processor, may also be adapted to perform a motion artifact correction compensation in the image based on the read-outs from the detector elements of the detector 8. According to an aspect of the present invention, this motion artifact compensation may be performed by determining a difference between a first ray and a second ray, wherein the first ray and the second ray are opposite rays and wherein the difference between the first ray and the second ray is due to the motion of an object of interest resulting in motion artifacts. In the following, the motion artifact may be compensated for on the basis of the determined difference, resulting in a motion artifact compensated projection data set. After that, the object of interest may be reconstructed from the motion artifact compensated projection data set, resulting in a motion artifact compensated image.

Furthermore, the calculation units may be adapted for performing a motion artifact compensation in the projection data sets of the object of interest by performing the following operation: loading the data set acquired by means of a rotating source of electromagnetic radiation generating a beam and by means of a radiation detector detecting the beam. After that, a difference between a first ray and a second ray is determined, wherein first and second rays are opposite rays and wherein the difference between the first and the second ray is due to the motion of the object of interest resulting in motion artifacts. First ray and second ray correspond to projection data of the projection data set. After that, the projection data set is compensated for a motion artifact on the basis of the difference, resulting in a motion artifact compensated projection data set. Following the compensation, a reconstruction of the object of interest from the motion artifact compensated projection data set may be performed, resulting in a motion artifact compensated image.

Furthermore, as may be taken from FIG. 1, the calculation unit 18 may be connected to a loudspeaker 21 to, for example, automatically output an alarm.

In the following, a short description of the basic formalism of several approximate helical cone-beam reconstruction algorithms is presented. The X-ray focus $\vec{a}(\lambda)$ is moving along a helical trajectory:

$$\vec{a}(\lambda) = (-R \cdot \cos \lambda, -R \cdot \sin \lambda, h\lambda + z_0)$$

The Pitch P is then $$P = 2\pi h.$$

Figure 2A:
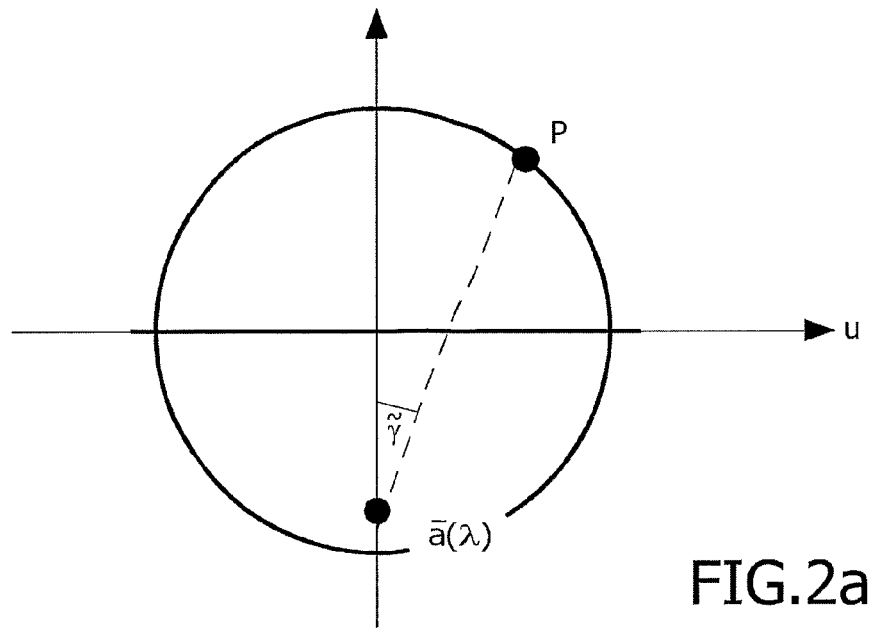

One possible detector is a virtual planar detector which is always perpendicular to the central ray and moves with the focus in the z-direction. It can be characterized for each focus-position $\lambda$ with two coordinates, u and v which are defined as follows (see FIG. 2a):

$$u = R \cdot \tan \gamma \quad v = z - h \cdot \lambda - z_0$$

This means that each projection value is characterized by the triple (u, v, $\lambda$). The virtual detector is spanned by two normal vectors $\vec{e}_u$ and $\vec{e}_v$ (pointing in the positive z-direction and is therefore $\vec{e}_z$). The vector $\vec{e}_f$ may be defined according to $$\vec{e}_f = \vec{e}_u \times \vec{e}_v$$

which is perpendicular to the virtual detector and points to the X-ray focus. Another virtual detector is the PI-window (or Tam-Danielsson window) which is delimited by two successive turns of the helix. It can be expressed by the coordinates of the virtual planar detector according to:

$$v_{Lower} \leq v \leq v_{Upper},$$

with

-continued $$v_{Upper,PI-Window} = h \cdot \left(1 + \frac{u^2}{R^2}\right) \cdot \left(\frac{\pi}{2} - \arctan\frac{u}{R}\right)$$

$$v_{Lower,PI-Window} = h \cdot \left(1 + \frac{u^2}{R^2}\right) \cdot \left(-\frac{\pi}{2} - \arctan\frac{u}{R}\right)$$

The PI-window guarantees a data acquisition scheme, which is in principle complete for an exact reconstruction of the object function, but also non-redundant.

The original PI-window may be generalized to the so called n-PI-window by a symmetric extension of the PI-window by one or more times the helical pitch. The upper and lower boundaries of the n-PI-window expressed by the coordinates of the virtual planar detector are:

$$v_{Upper,n-PI-Window} = h \cdot \left(1 + \frac{u^2}{R^2}\right) \cdot \left(\frac{n\pi}{2} - \arctan\frac{u}{R}\right)$$

$$v_{Lower,n-PI-Window} = h \cdot \left(1 + \frac{u^2}{R^2}\right) \cdot \left(-\frac{n\pi}{2} - \arctan\frac{u}{R}\right)$$

The importance of the PI and the n-PI window is due to the fact that from all projection data measured at a certain source position λ, only the data, which are located on the lower or upper boundary of these windows are also measured from the opposite direction. Thus, only these data are used in the present invention to detect motion.

The PI-FBP Algorithm

Figure 2B:
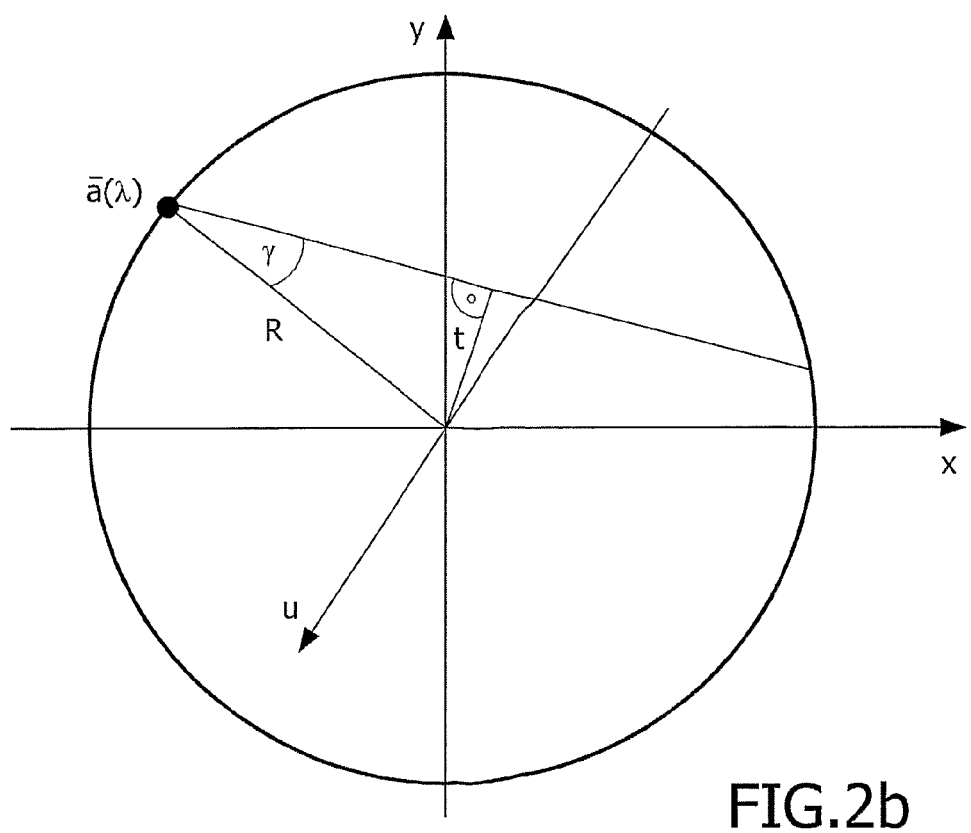

The PI-Filtered back-projection Algorithm (PI-FBP Algorithm) is an approximate reconstruction algorithm for a helical trajectory. It works in principle like that:

it operates only on projection data in the PI-window
the data are rebinned into parallel beam geometry
pre-weighting of the rebinned data with the cosine of the cone-angle (this compensates the different path lengths of the X-rays and guarantees that objects which are homogeneous in z-direction can be exactly reconstructed)
ramp filtering row by row
back-projection of the filtered projection data The rebinning of the data corresponds to a change in the coordinate systems, expressed by $$(u, v, \lambda) \Leftrightarrow (t, \theta, s)$$

with (see FIG. 2b)

$$t = R \cdot \sin\gamma = \frac{-u}{\sqrt{1 + \frac{u^2}{R^2}}}$$

$$\theta = \lambda + \gamma = \lambda - \arctan\left(\frac{u}{R}\right)$$

$$s := z - h \cdot \theta - z_0 = \frac{v}{\left(1 + \frac{u^2}{R^2}\right)} + h \cdot \arctan\left(\frac{u}{R}\right).$$

In the above formulas, γ is the fan angle, t is the distance of the line integral to the z-axis when projected into the x-y-plane and θ is the angle between this line-integral and the x-axis. A short calculation shows that the s-coordinates of the upper and lower boundaries of the n-PI-window are:

$$s_{Upper,n-PI-window} = \frac{n\pi h}{2} \quad \text{(Equation (1))}$$

and $$s_{Lower,n-PI-window} = -\frac{n\pi h}{2}$$

with $$s \in \left[-\frac{n\pi}{2}h; \frac{n\pi}{2}h\right] \text{ for the } n - PI - \text{window}.$$

As was already mentioned, after rebinning into parallel beam geometry, the projection data are weighted with the cosine of the cone angle κ which is:

$$\cos\kappa = \frac{\sqrt{R^2 - t^2}}{\sqrt{R^2 - t^2 + (s + h \cdot \gamma)^2}}$$

Afterwards, the data are ramp-filtered in the t-direction (as in 2D-parallel beam reconstruction). At the end, for each voxel with the coordinates (x, y, z) a back-projection is done to compute the object function g(x,y,z):

$$g(x, y, z) = \frac{1}{N_\theta} \sum_{n=n_{Sunrise}(x,y,z)}^{n_{sunrise}+N_\theta-1} p_{Filtered,Parallel}(t(x, y, \theta_n), \theta_n, s(x, y, z, \theta_n))$$

Figure 3:
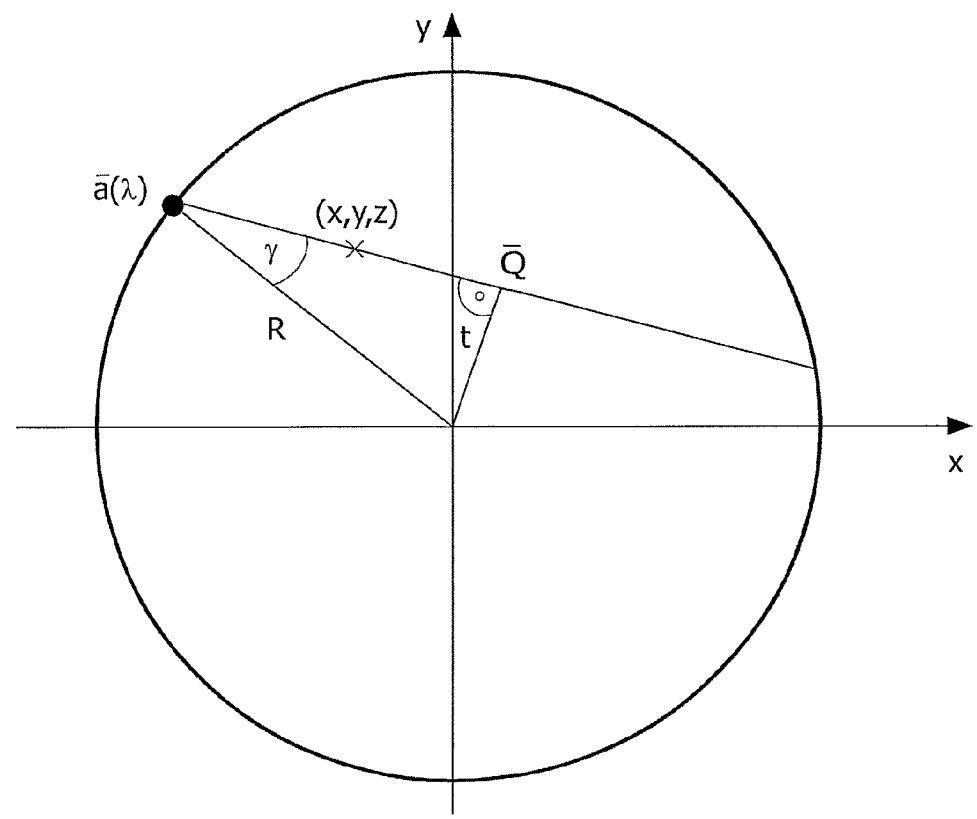
FIG. 3 shows a geometry for back-projection according to a PI-FBP algorithm.

The following relations are given (see FIG. 3):

$$\gamma = \arctan\left(\frac{-x \cdot \sin\lambda + y \cdot \cos\lambda}{R + x \cdot \cos\lambda + y \cdot \sin\lambda}\right)$$

$$\gamma = \arcsin\left(\frac{t}{R}\right)$$

$$\theta = \lambda + \gamma$$

$$t = -x \cdot \sin\theta + y \cdot \cos\theta$$

The distance μ from (x,y,z) to the point $\vec{Q}$ is:

$$\mu(x,y,\theta) = x \cdot \cos\theta + y \cdot \sin\theta$$

Figure 4:
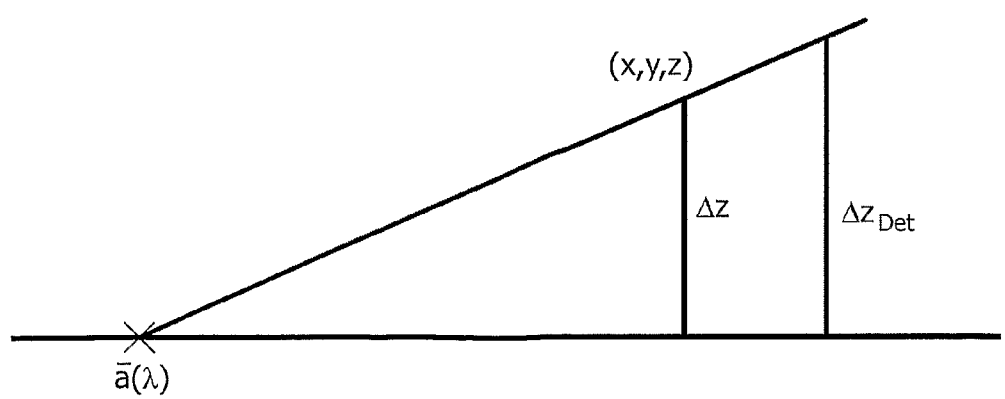
FIG. 4 shows a geometry for determining s according to a PI-FBB algorithm.

For the s-coordinate, the following relations are given (see FIG. 4):

$$\frac{\Delta z}{\Delta z_{Det}} = \frac{\sqrt{R^2 - t^2} + \mu(x, y, \theta)}{\sqrt{R^2 - t^2}},$$

$$\Delta z = z - h\lambda - z_0,$$

$$s = z - h\theta - z_0 = \Delta z_{Det} - h\gamma,$$

and therefore:

$$s = -h\gamma + \frac{(z - h\lambda - z_0) \cdot \sqrt{R^2 - t^2}}{\sqrt{R^2 - t^2} + x \cdot \cos\theta + y \cdot \sin\theta}.$$

For every voxel, the back-projection may only be performed for x-rays belonging to the PI-window which corresponds to an angular range of Δθ=π. This means that one has to calculate for every voxel when the X-ray (so called PI-line) enters the PI-window (for this PI-line we have s=hπ/2) and determine its coordinates (t, θ, s)$_{SR}$ where SR stands for sunrise. The same PI-line exists for the "sunset" (X-ray leaves the PI-window), with θ$_{SS}$=θ$_{SR}$+π, t$_{SS}$=−t$_{SR}$ and s$_{SS}$=−hπ/2.

The WEDGE-Algorithm

The WEDGE-Algorithm is also an approximate reconstruction algorithm for a helical trajectory. It works in principle like that:

the data are rebinned into parallel beam geometry (but different when compared with the PI-FBP algorithm, see below)

pre-weighting of the rebinned data with the cosine of the cone-angle (this compensates the different path lengths of the X-rays and guarantees that objects which are homogeneous in z-direction can be exactly reconstructed)

ramp filtering row by row back-projection of the filtered projection data

The rebinning of the data into parallel beam geometry is identical with the PI-FBP algorithm. However, it is different with respect to the coordinate describing the detector height. For the PI-FBP algorithm we already have shown the coordinate transformation from a virtual planar detector to the PI-Geometry:

$$(u, v, \lambda) \Leftrightarrow (t, \theta, s)$$

For the WEDGE-algorithm, the corresponding coordinate transformation is:

$$(u, v, \lambda) \Leftrightarrow (t, \theta, v_W)$$

Figure 5:
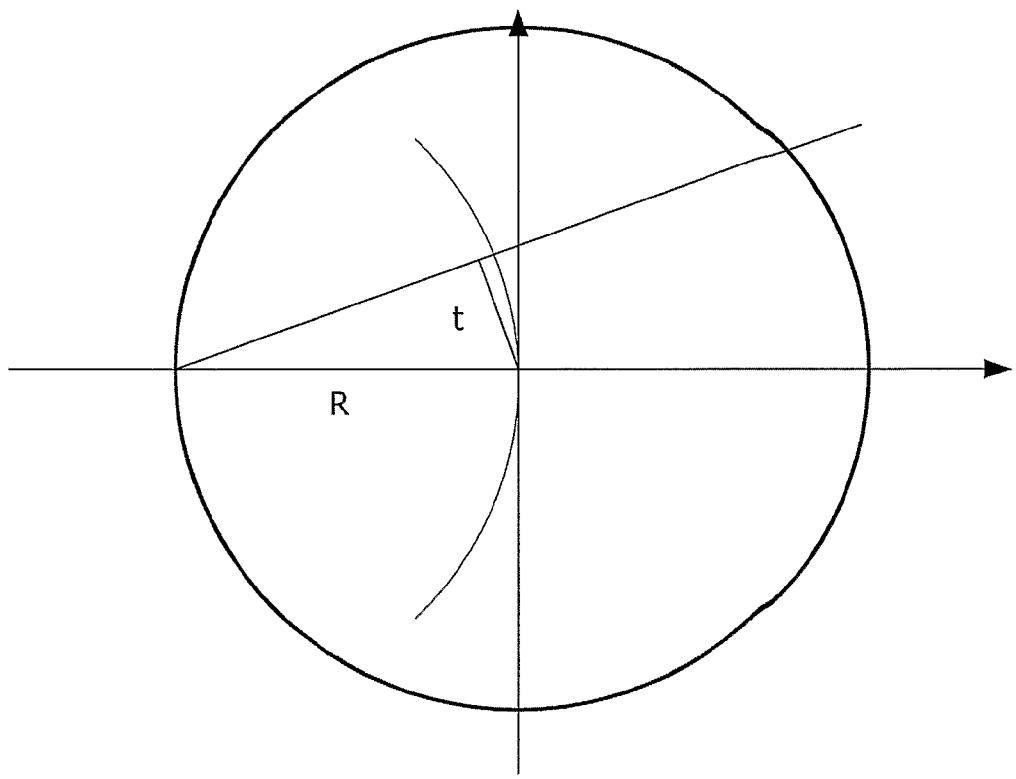
FIG. 5 shows a schematic representation of a virtual focus-centered detector.
Figure 6:
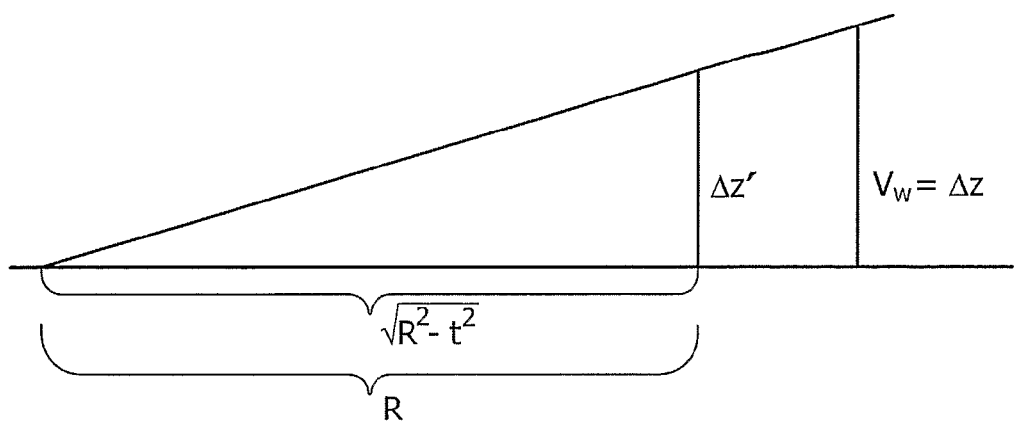
FIG. 6 shows the geometry for determining $V_w$ according to a WEDGE algorithm.

The remaining transformation $v_w(u,v,\lambda)$ may be derived from the following relations (see FIG. 5 and FIG. 6):

$$v_W = \Delta z = z - h\lambda - z_0$$

$$\Delta z' = z' - h\lambda - z_0$$

$$\frac{v_W}{\Delta z'} = \frac{R}{\sqrt{R^2 - t^2}}$$

$$v_w = (z' - h\theta - z_0)\frac{R}{\sqrt{R^2 - t^2}}$$

The following relation between s in the PI-FBP geometry and $v_W$ in the WEDGE geometry is obtained:

$$s\frac{R}{\sqrt{R^2 - t^2}} = v_w \quad \text{(Equation (2))}$$

Figure 7:
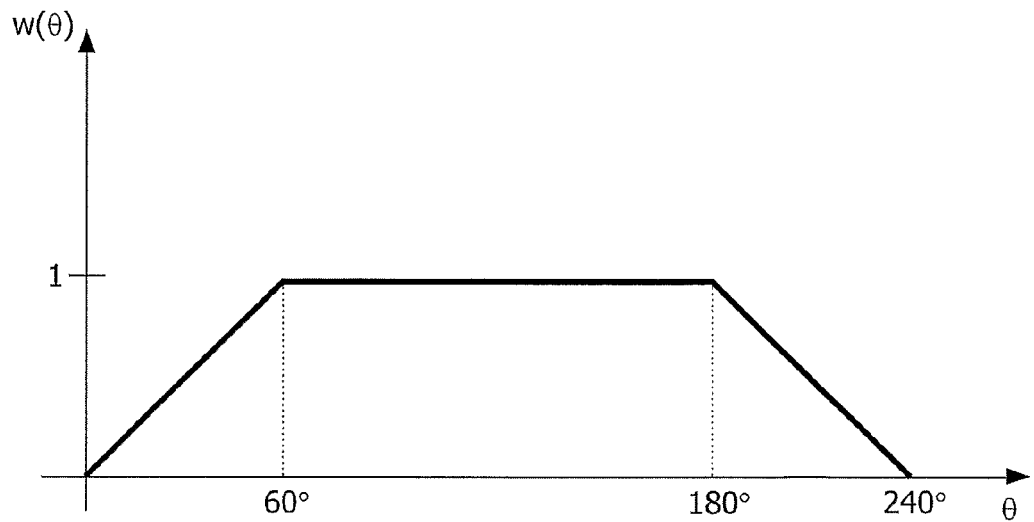
FIG. 7 shows an example of a weighting function w(Θ).

As for the PI-FBP algorithm, after rebinning into the WEDGE beam geometry, there is a pre-weighting of the projection data with the cosine of the cone angle to guarantee an exact reconstruction for objects, which are homogeneous in the z-direction. Afterwards, the ramp filtering in t-direction is applied. At the end, the back-projection is done for every voxel (x,y,z) with the filtered projection data. For the WEDGE algorithm, the back-projection is done over the whole detector height, not just the PI-window. This means that the angular range Δθ is usually larger than π. As an immediate consequence, there must be a weighting function w(θ) which is used during the back-projection process and which compensates for the fact that some rays are twice present and others only once (see FIG. 7). However, one must be aware that such a weighting function may be problematic since two rays which differ in θ by π are not really parallel to each other. As a consequence, for objects with strong gradients in z-direction, the WEDGE algorithm usually shows more artifacts in the reconstructed image than the PI-FBP algorithm.

WEDGE-PI Algorithm

The WEDGE-PI algorithm is nearly identical to the WEDGE-Algorithm, but uses only projection data in the PI-window. The difference with respect to the PI-FBP method is the filtering.

As already mentioned, the projection data in the PI-window are in principle sufficient for an exact reconstruction of the measured object, but also non-redundant. This means that in principle no weighting of the projection data has to be done which compensates for the fact that some line integrals are measured more than once.

However, reconstruction algorithms which operate solely on the PI-window are much more sensitive to motion artifacts. During the back-projection process, the first and the last ray (PI-line of the "sunrise" and PI-line of the "sunset") are identical and should contain the same projection values. This is not true anymore, when motion is happening. This inconsistency in the projection values immediately manifests itself in streaking artifacts in the reconstructed image.

Algorithms which perform the back-projection over an angular range larger than π are much less sensitive to motion artifacts. The reason is that the inconsistencies in the projection data set are somehow smeared out onto a larger areas in the reconstructed image and therefore not as easily visible (no distinct streaks).

In order to improve image quality it may be advisable to use a "larger" back-projection window (larger than the PI-window) in image areas where motion has happened, but to use a relatively "small" angular range for the back-projection (PI-window or at least not substantially larger than PI-window) when the motion is "not so strong". A motion-detecting algorithm and subsequent adaptation of the angular range for the back-projection (WEDGE-PI+Epsilon Algorithm) according to an exemplary embodiment of the present invention comprises the following steps:

for every voxel (x,y,z) the PI-lines for sunrise and sunset are determined if the projection values for the PI-lines are (nearly) identical, one takes the PI-window for back-projection if the projection values for the PI-lines are rather different, one takes the full angular range (over the full detector height) for back-projection.

In the following, the WEDGE-PI+Epsilon Algorithm will be described in more detail. The algorithm works on projection data in WEDGE-geometry.

Ideally, for a non-moving object the projection values of the PI-Lines of every voxel should be the same:

$$p(t, \theta, v_w(s=\pi h/2)) = p(-t, \theta+\pi, v_w(s=-\pi h/2))$$

(see equations (1) and (2)). In reality, they are not the same and one can define the relative deviation of the projection values of the PI-Lines of every voxel:

$$d_{Rel}(\vec{r}) := \frac{|p(t, \theta, v_w(s = \pi h/2)) - p(-t, \theta + \pi, v_w(s = -\pi h/2))|}{\max(p(t, \theta, v_w(s = \pi h/2)), p(-t, \theta + \pi, v_w(s = -\pi h/2))}.$$

In the following, this quantity is called "PI-Line-Deviation".

The program, according to an exemplary embodiment of the present invention, may now loop over all voxels which have to be reconstructed. As already mentioned above, for each voxel the values of t, θ, and $v_w$ corresponding to the sunrise of the PI-window are calculated. Calculating a projection value at these coordinates may generally require a three-dimensional interpolation since the real data are sampled discretely in all coordinates. In the following embodiment, a tri-linear interpolation is used.

The angular range for the back-projection of every voxel is adjusted individually by choosing two thresholds $\tau_1$ and $\tau_2$:

if $d_{Rel}(x,y,z) \leq \tau_1$, one chooses $\Delta\theta(x,y,z) = \pi + \epsilon_1$
if $d_{Rel}(x,y,z) \geq \tau_2$, one chooses $\Delta\theta(x,y,z) = \pi + \epsilon_2$
if $\tau_1 \leq d_{Rel}(x,y,z) \leq \tau_2$, one chooses $$\Delta\theta(x, y, z) = \pi + \epsilon_1 + \frac{(d_{Rel} - \tau_1)}{(\tau_2 - \tau_1)} \cdot (\epsilon_2 - \epsilon_1).$$

As an alternative, $\pi + \epsilon_2$ may be replaced by the angular range provided by the WEDGE algorithm (the default "Overscan" window).

Figure 8:
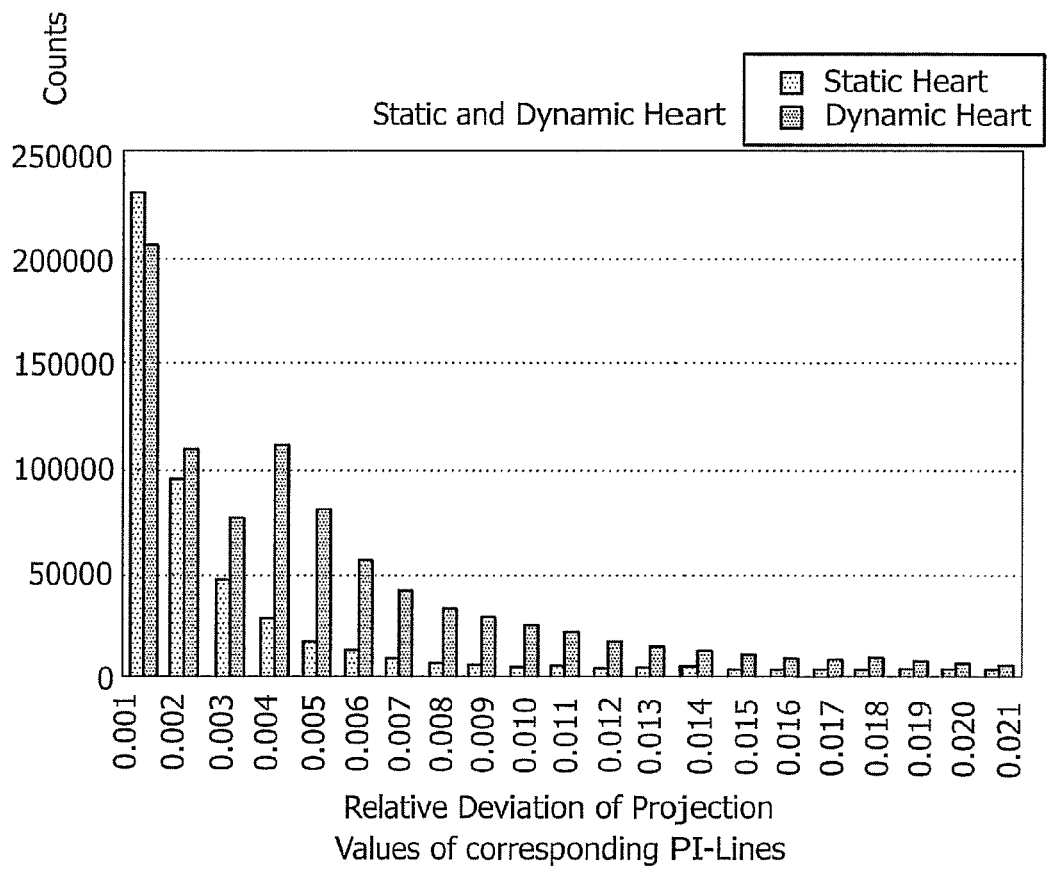
FIG. 8 shows a histogram of a PI-line-deviation for a moving (dynamic) and non-moving (static) heart.
Figure 9:
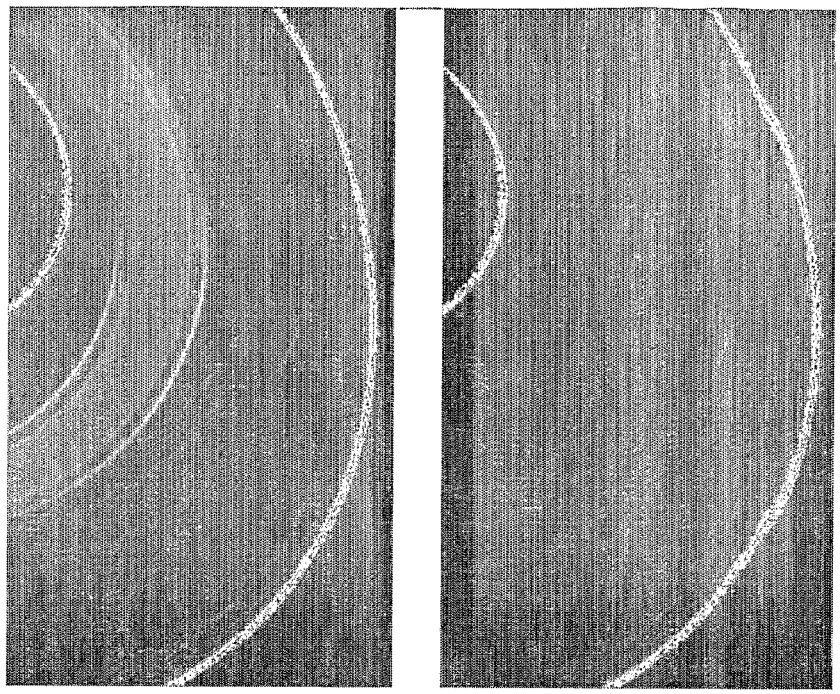
FIG. 9 shows PI-line deviations for a moving heart (left image) and a non-moving heart (right image) in the form of an axial slice.

For the thorax phantom a histogram depicting the relative PI-Line deviations for the moving and non-moving heart is shown in FIG. 8. The motion-induced PI-Line deviations are between 0.3% and 2%. Therefore, as already mentioned above, a careful determination of the PI-Lines and their corresponding projection values may be mandatory so that the "signal" ($d_{Rel}$) may be separated from "discretization noise". FIG. 9 shows the PI-Line-deviations for one axial slice for the moving heart (left image) and non-moving heart (right image). The effect of the moving heart is obvious.

FIG. 10a shows a reconstructed axial slice for a moving heart, which is not compensated for motion artifacts according to the present invention. On the left side of the picture, e.g., stripes resulting from a motion of parts of the heart can clearly be identified. Furthermore, a pronounced shadow artifact near the vertebra is present.

FIG. 10b shows two reconstructed axial slices for a moving heart, compensated for motion artifacts according to an exemplary embodiment of a method according to the present invention, where $\epsilon_1$ was chosen as 30° and the angular range was adjusted in the interval [$\pi+\epsilon_1$;Overscan] with the parameters $\tau_1$=0.0025 and $\tau_2$=0.02. The motion artifacts are clearly suppressed (left image of FIG. 10b); furthermore, there is no pronounced shadow artifact near the vertebra present (right image of FIG. 10b).

FIG. 11 shows a schematic PI measurement geometry of a CT scanner system for performing the method according to an exemplary embodiment of the present invention. For an exact PI reconstruction algorithm, a detector area is used, which corresponds to the detector area depicted in FIG. 11, fitting between one cycle of the radiation source, which moves along a helical path around the object of interest and which emits a cone beam of polychromatic radiation. PI-lines are located at the upper and lower boundaries of the detector 30. At position 34, the source 4 emits a beam, which comprises a first ray 32, striking a certain object point 33 and hitting detector 30 at position 35. After half a revolution of the source 4 along the helical path 31 to position 35, the source 4 emits a cone beam, which comprises a second ray 36, running from position 35 of source 4, past object points 33 to position 34, which is now located on the detector 30. Therefore, the rays 32 and 36, which are emitted at different times from different sides of the helical path are true opposite arrays.

FIG. 12 shows a schematic 3-PI measurement geometry for a CT scanner system for performing a method according to an exemplary embodiment of the present invention. The radiation source 4 moves along helical path 31 and emits a cone beam of electromagnetic radiation. At position 34, the source 4 emits a cone beam which comprises the first ray 32, passing the object point 33 and hitting the detector 30 at position 35. After one and a half revolutions of the source 4 along the helical path 31, the source is positioned at point 35 and emits a cone beam, comprising the second ray 36, which passes the object point 33 and hits the detector 30 at position 34. Since the detector 30 moves along the helical path 31 and is always opposite radiation source 4, the detector 30 is located on the opposite side of its position depicted in FIG. 12, when source 4 has been moved to position 35. Therefore, the first ray 32 and the second ray 36 are opposite rays, passing the same object point 33 and may therefore be used for motion detection and compensation of a motion artifact arising from a motion of object point 33 according to a method of an exemplary embodiment of the present invention.

FIG. 13 shows a flow-chart of an exemplary embodiment of a method of motion artifact compensation according to the present invention. After the start in step S1, an acquisition of the projection data set is performed in step S2. After that, the acquired data set is loaded into the memory of a data processor and a first ray and a second ray are selected in step S3, wherein the first ray and the second ray are selected on the basis of the projection data. After that, in step S4, it is determined whether the difference between the first ray and the second ray is greater than a predetermined threshold value. The threshold value may be set by a user or it may be set from the software side, depending on properties of the projection data. If the difference between the first ray and the second ray is not significant, meaning that it is less than or equal to the predetermined threshold value, no motion artifact correction is performed (step S5). On the other hand, if the difference between the first ray and the second ray is greater than the predetermined threshold value, a motion artifact compensation is performed in step S6 by low-pass filtering. Advantageously, the first ray or the second ray may be interpolated from adjacent rays, for example, if no original second ray may be found which is opposite to the first ray. In other words, if a motion artifact results from a motion of an object point which is passed by the first ray and the second ray, the motion artifact may be compensated for by a low-pass filtering of the projection data in the region of the motion artifact before the reconstruction of the first object point by an exact reconstruction algorithm. Then, in step S7, a reconstruction of the object point is performed by the exact reconstruction algorithm, which may use, according to an exemplary embodiment of the present invention, projection data resulting from half a revolution (PI) or three half revolutions (3-PI) of the radiation source.

Furthermore, the characteristics of the low-pass filtering, such as filter strength and frequency dependence, may, according to an exemplary embodiment of the present invention, correspond to properties of the projection data in the region of the motion artifact. In other words, the low-pass filtering may be performed in regions where motion has been detected in an adaptive manner.

The motion artifact compensation method ends in step S8.

FIG. 14 shows a flow-chart of another exemplary embodiment of a method of motion artifact compensation according to the present invention. The method of motion artifact compensation starts with step S1. The acquisition of a projection data set of the object of interest by means of a source of electromagnetic polychromatic radiation generating a cone beam and by means of a radiation detector detecting the cone beam is performed in step S2. After that, in step S3, a first ray and a second ray are selected, wherein the first ray and the second ray correspond to projection data of the projection data set and wherein the first ray and the second ray are opposite rays. After that, in step S4, the first ray and the second ray are compared to each other and it is determined whether there is a significant difference between the first ray and the second ray. If there is no significant difference between the two opposing rays, no motion artifact correction is performed (step S5). On the other hand, if a significant difference between the first ray and the second ray has been detected, the over-scan range is increased, leading to a motion artifact compensation in the data corresponding to the first ray and the second ray. This is performed in step S6.

It should be noted that the object of interest, which is scanned by the CT scanner system, comprises a plurality of object points. One of these object points, the first object point, is passed by both the first ray and the second ray. The reconstruction of the first object point is performed by an approximate reconstruction algorithm, wherein an over-scan range is used for reconstruction of the first object point. By increasing the over-scan range of the object point, a suppression of motion artifacts may be increased. Therefore, if a difference between the first ray and the second ray exceeds a certain predetermined threshold value, the corresponding projection data is considered to comprise motion artifacts resulting from a motion of the first object point. In consequence, the motion artifact is compensated for by increasing the over-scan range of the first object point. Advantageously, the amount of the increase of the over-scan range corresponds to properties of the projection data in the region of the motion artifact. Therefore, the over-scan range used for reconstruction of an object point may be increased adaptively, depending on the properties of the projection data. This procedure may allow for a local optimization of the image quality.

After that, in step S7, a reconstruction of the object of interest is performed by an approximate reconstruction algorithm, such as a WEDGE algorithm, a WEDGE–PI algorithm, a WEDGE-PI+Epsilon algorithm or a PI-filtered-back projection algorithm, which are described above in more detail.

The method ends in step S8.

FIG. 15 depicts an exemplary embodiment of an image processing device according to the present invention, for executing an exemplary embodiment of a method in accordance with the present invention. The image processing device depicted in FIG. 15 comprises a central processing unit (CPU) or image processor 151 connected to a memory 152 for storing an image depicting the object of interest, such as a patient. The image processor 151 may be connected to a plurality of input/output network or diagnosis devices, such as an MR device or a CT device. The image processor is furthermore connected to a display device 154, for example, a computer monitor, for displaying information or image computed or adapted in the image processor 151. An operator may interact with the image processor 151 via a keyboard 155 and/or other output devices, which are not depicted in FIG. 15.

Furthermore, via the bus system 153, it is also possible to connect the image processing and control processor 151 to, for example, a motion monitor, which monitors a motion of the object of interest. In case, for example, a lung of a patient is imaged, the motion sensor may be an exhalation sensor. In case the heart is imaged, the motion sensor may be an electrocardiogram (ECG).

The invention claimed is:

1. A method of motion artifact compensation in a projection data set of an object of interest, wherein the projection data set is acquired by means of a source of electromagnetic radiation generating a beam and by means of a radiation detector detecting the beam, the method comprising the steps of:
 selecting projection data corresponding to a first ray and a second ray from the projection data set;
 wherein the first and second rays are diametrically opposed rays passing through a same object point;
 determining a difference of the projection data corresponding to the first and second rays;
 wherein the difference is indicative of motion of the object of interest corresponding to motion artifacts;
 generating a motion artifact compensated data set by compensating the projection data set for the motion artifacts on the basis of the difference; and
 generating a motion artifact compensated image by reconstructing the object of interest from the motion artifact compensated projection data set.

2. The method according to claim 1, wherein the determination of a difference between the first ray and the second ray further comprises the steps of:
 determining whether the difference between the first ray and the second ray is bigger than a predetermined threshold; and
 compensating the projection data set for a motion artifact if the difference is bigger than the predetermined threshold.

3. The method according to claim 1, wherein the second ray is interpolated from adjacent rays.

4. The method according to claim 1,
 wherein the object of interest comprises a plurality of object points;
 wherein a reconstruction of a first object point of the plurality of object points is performed by an exact reconstruction algorithm; and
 wherein, if the motion artifact results from a motion of the first object point, the motion artifact is compensated for by a low pass filtering of the projection data in the region of the motion artifact before the reconstruction of the first object point by the exact reconstruction algorithm.

5. The method according to claim 4,
 wherein the source of radiation moves around the object of interest; and
 wherein the exact reconstruction algorithm uses projection data resulting from one of no more than half a revolution and three half revolutions of the source of radiation.

6. The method according to claim 4, wherein characteristics of the low pass filtering correspond to properties of the projection data in the region of the motion artifact.

7. The method according to claim 1,
 wherein the object of interest comprises a plurality of object points;
 wherein a reconstruction of a first object point is performed by an approximate reconstruction algorithm;
 wherein an over-scan range is used for reconstruction of the first object point; and
 wherein, if the motion artifact results from a motion of the first object point, the motion artifact is compensated for by increasing the over-scan range.

8. The method according to claim 7,
 wherein the first object point belongs to a PI-line on which motion has been detected; and
 wherein the increase of the over-scan range corresponds to properties of the projection data in the region of the motion artifact.

9. The method according to claim 7, wherein the approximate reconstruction algorithm is one of a WEDGE algorithm and a PI-filtered back-projection algorithm.

10. The method according to claim 1,
wherein the source of electromagnetic radiation is a polychromatic x-ray source;
wherein the source moves along a helical path around the object of interest; and
wherein the beam has one of a cone beam and a fan beam geometry.

11. The method according to claim 1, wherein the first ray and the second ray are not opposite adjacent rays.

12. The method according to claim 1, wherein the radiation detector at a first projection angle is not offset from the radiation detector at a second projection angle 180° from the first projection angle.

13. A data processing device comprising:
a memory for storing a data set;
a data processor for performing motion artifact compensation in a projection data set of an object of interest, wherein the data processor is adapted for performing the following operation:
loading the projection data set acquired by means of a rotating source of electromagnetic radiation generating a beam and by means of a radiation detector detecting the beam;
wherein projection data corresponding to a first ray and a second ray is selected from the projection data set and the first and second rays are diametrically opposed rays passing through a same object point;
determining a difference of the projection data corresponding to the first and second rays;
wherein the difference is indicative of motion of the object of interest corresponding to motion artifacts;
generating a motion artifact compensated data set by compensating the projection data set for the motion artifacts on the basis of the difference; and
generating a motion artifact compensated image by reconstructing the object of interest from the motion artifact compensated projection data set.

14. A computer-readable medium storing a computer program for performing motion artifact compensation in a projection data set of an object of interest, wherein the computer program causes a processor to perform the following operation when the computer program is executed on the processor:
loading the projection data set acquired by means of a rotating source of electromagnetic radiation generating a beam and by means of a radiation detector detecting the beam;
wherein projection data corresponding to a first ray and a second ray is selected from the projection data set and the first and second rays are diametrically opposed rays passing through a same object point;
determining a difference of the projection data corresponding to the first and second rays;
wherein the difference is indicative of motion of the object of interest corresponding to motion artifacts;
generating a motion artifact compensated image by compensating the projection data set for the motion artifacts on the basis of the difference; and
generating a motion artifact compensated image by reconstructing the object of interest from the motion artifact compensated projection data set.

15. The computer-readable medium of claim 14, wherein determining a difference between the first ray and the second ray further comprises:
determining whether the difference between the first ray and the second ray is bigger than a predetermined threshold; and
compensating the projection data set for a motion artifact if the difference is bigger than the predetermined threshold.

16. The computer-readable medium of claim 14, wherein the second ray is interpolated from adjacent rays.

17. The computer-readable medium of claim 14,
wherein the object of interest comprises a plurality of object points;
wherein a reconstruction of a first object point of the plurality of object points is performed by an exact reconstruction algorithm; and
wherein, if the motion artifact results from a motion of the first object point, the motion artifact is compensated for by a low pass filtering of the projection data in the region of the motion artifact before the reconstruction of the first object point by the exact reconstruction algorithm.

18. The computer-readable medium of claim 17,
wherein the source of radiation moves around the object of interest; and
wherein the exact reconstruction algorithm uses projection data resulting from one of no more than half a revolution and three half revolutions of the source of radiation.

19. The computer-readable medium of claim 17, wherein characteristics of the low pass filtering correspond to properties of the projection data in the region of the motion artifact.

20. The computer-readable medium according to claim 14,
wherein the object of interest comprises a plurality of object points;
wherein a reconstruction of a first object point is performed by an approximate reconstruction algorithm;
wherein an over-scan range is used for reconstruction of the first object point; and
wherein, if the motion artifact results from a motion of the first object point, the motion artifact is compensated for by increasing the over-scan range.

* * * * *